United States Patent [19]

Shah

[11] Patent Number: 5,693,327

[45] Date of Patent: Dec. 2, 1997

[54] HERBAL COMPOSITIONS

[76] Inventor: Eladevi Shah, 50 Elm Croft Crescent, London NW11 9SY, United Kingdom

[21] Appl. No.: 501,598

[22] Filed: Jul. 12, 1995

[51] Int. Cl.$^6$ ................................................ A61K 35/78
[52] U.S. Cl. .................. 424/195.1; 514/861; 514/863
[58] Field of Search .................... 424/195.1; 514/861, 514/863

[56] References Cited

U.S. PATENT DOCUMENTS

| | | | |
|---|---|---|---|
| 4,515,785 | 5/1985 | Shimizu et al. | 424/195.1 |
| 4,536,496 | 8/1985 | Shimizu et al. | 514/54 |
| 4,537,774 | 8/1985 | Shimizu et al. | 424/195.1 |
| 5,196,197 | 3/1993 | Talwar et al. | 424/195.1 |

OTHER PUBLICATIONS

Chem. abstr., vol. 99, 1983, (Solumbus, OH, USA), p. 93, col. 2, the abstract No. 72536w, Batra, A., et a., 'Centratherum anthelminticum–identification of the fatty acid composition and antimicrobial activity of the oil.' Fette, Seifen, Anstrichm. 85, 1983.

*Primary Examiner*—John W. Rollins
*Attorney, Agent, or Firm*—Kubovcik & Kubovcik

[57] ABSTRACT

The present invention relates to the preparation and use of compositions for the treatment of skin disorders such as psoriasis, eczema and lichen planus, as well as for the promotion of good health and the alleviation of stress. The compositions are based on extracts from the plants *Melia azadirachta* and/or *Centratherum anthelminthicum*. A variety of other herbal extracts may be included, and the compositions may take the form of a cream or ointment based on ghee, or they may be in a powdered form of suitable for preparing decoctions in hot water.

13 Claims, No Drawings

HERBAL COMPOSITIONS

BACKGROUND OF THE INVENTION

This invention relates to the manufacture and use of herbal compositions for the treatment of skin conditions and/or the promotion of general good health, and in particular, but not exclusively, for the treatment of psoriasis, eczema and lichen planus in human and non-human animals.

The skin of an animal acts as a barrier between the organism and its environment, and thus preserves the chemical and biochemical composition of the body of the animal. However, various chemical and physical agents may have effects, good or bad, on the skin.

The chemical composition and physical structure of the skin departs significantly from normal conditions in certain skin diseases such as psoriasis, eczema and lichen planus. For example, the epidermis contains a constantly renewing cell population. In humans, the transit time of cells from the inner part to the outermost part of the skin is in the order of 12 to 14 days from mitosis to the viable epidermis and about 15 days across the stratum corneum; i.e. around 28 days in total. In a human suffering from psoriasis, however, the total transit time may be as short as 4 days. Psoriasis is classified as a proliferative skin disease, since one of the manifestations of the condition is a proliferation in keratinocyte activity. Psoriasis is also characterised by an aberration of lipid metabolism, due at least in part to excessive lipoxygenase activity in the epidermis.

SUMMARY OF THE INVENTION

According to a first aspect of the present invention, there is provided a composition for use in the treatment of skin disorders and/or promoting general health, which composition comprises extracts derived from the plant *Melia azadirachta*.

According to a second aspect of the present invention, there is provided a composition for use in the treatment of skin disorders and/or promoting general health, which composition comprises extracts derived from the plant *Centratherum anthelminthicum*.

According to a third aspect of the present invention, there is provided a composition for use in the treatment of skin disorders and/or promoting general health, which composition comprises extracts derived from the plants *Melia azadirachta* and *Centratherum anthelminthicum*.

According to a fourth aspect of the present invention, there is provided a composition for use in the treatment of skin disorders and/or promoting general health, which composition comprises extracts derived from at least one member of the group consisting of the plants *Melia azadirachta* and *Centratherum anthelminthicum*, and which further comprises extracts derived from at least one member of the group consisting of the plants *Phyllanthus emblica, Hemidesmus indicus, Tinospora cordifolia, Curcuma longa, Terminalia chebula, Terminalis belerica, Berberis aristata, Zingiber officinalis, Piper longum, Piper nigrum, Rubia cordifolia, Smilex china, Glycerhiza glabra, Picrorhiza curroa, Curcuma aromatica* and *Asparagus racemosus*.

The composition may further comprise coffee and/or cardamon seeds.

According to a fifth aspect of the present invention, there is provided a method of treating psoriasis through the administration of extracts derived from at least one member of the group consisting of the plants *Melia azadirachta* and *Centratherum anthelminthicum*.

According to a sixth aspect of the present invention, there is provided a method of treating psoriasis through the administration of extracts derived from at least one member of the group consisting of the plants *Melia azadirachta* and *Centratherum anthelminthicum* and further extracts derived from at least one member of the group consisting of the plants *Phyllanthus emblica, Hemidesmus indicus, Tinospora cordifolia, Curcuma longa, Terminalia chebula, Terminalis belerica, Berberis aristata, Zingiber officinalis, Piper longum, Piper nigrum, Rubia cordifolia, Smilex china, Glycerhiza glabra, Picrorhiza curroa, Curcuma aromatica* and *Asparagus racemosus*.

According to a seventh aspect of the present invention, there is provided a method of treating eczema or lichen planus through the administration of extracts derived from at least one member of the group consisting of the plants *Melia azadirachta* and *Centratherum anthelminthicum*.

According to an eighth aspect of the present invention, there is provided a method of treating eczema or lichen planus through the administration of extracts derived from at least one member of the group consisting of the plants *Melia azadirachta* and *Centratherum anthelminthicum* and further extracts derived from at least one member of the group consisting of the plants *Phyllanthus emblica, Hemidesmus indicus, Tinospora cordifolia, Curcuma longa, Terminalia chebula, Terminalis belerica, Berberis aristata, Zingiber officinalis, Piper longum, Piper nigrum, Rubia cordifolia, Smilex china, Glycerhiza glabra, Picrorhiza curroa, Curcuma aromatica* and *Asparagus racemosus*.

The composition of the present invention may be dispersed in a suitable carrier for topical application as a cream, gel, ointment or lotion, or may be in the form of a dry powder or other form suitable for the preparation of a potable decoction, for example by way of a tea bag. Alternatively, the composition may be formulated in tablet form.

Preferably, the composition is dispersed in a carrier suitable for topical application comprising ghee or clarified butter.

By providing one or more of an anti-histaminic agent, an anti-inflammatory agent, an adrenocortical stimulant, a cortisol protecting agent, a keratolytic agent, an anti-infective agent, an anti-fungal agent, an agent to control any over-drying action and an agent to control any over-secretory action, the compositions of the present invention help to break the cycle of pruritus—inflammation—pruritus, thereby promoting faster healing of chronic skin conditions such as eczema, psoriasis and lichen planus. The compositions of the present invention are additionally useful in reducing the effects of stress and reinforcing the immune response. In particular, extracts from *Melia azadirachta* and *Centratherum anthelminthicum* are effective in inhibiting keratinocyte proliferation, and extracts from *Melia azadirachta* and *Curcuma longa* are effective inhibitors of lipoxygenase enzyme.

The transformed human keratinocyte cell line SVK14 was exposed to herbal extracts according to the present invention, and proliferation was measured indirectly using a colorimetric assay for determining the cellular protein content of adherent cultures in 96-well microtitre plates. *Melia azadirachta* L. (Meliaceae) and *Centratherum anthelminthicum* (Wild.) Kuntze (Compositae) were found to have a significant inhibitory effect on keratinocyte proliferation, having the IC50 values of 0.45 mg/ml and 0.5 mg/ml respectively. The IC50 values are based on the original dried plant material used for the extraction. The activity was dose-dependent.

DETAILED DESCRIPTION OF THE PREFERRED EMBODIMENT

A particularly preferred embodiment of the present invention is a cream made up as follows:

| | |
|---|---|
| Ghee | 3 kg |
| Water (boiled and cooled) | 1 kg |
| Decoction of *Centratherum anthelminthicum* (400 ml water + 40 g *Centratherum anthelminthicum*) | 400 ml |
| Decoction of *Melia azadirachta* (100 ml water + 250 g *Melia azadirachta*) | 100 ml |

To make up the cream, the ghee is first hydrolysed in a clean stainless steel vessel with one liter of water. Two to three days later, further hydrolysis should be effected with the decoction of *Centratherum anthelminthicum*. After a further two to three days, hydrolysis should be effected with the decoction of *Melia azadirachta*. The cream is ready when it becomes unable to assimulate any further liquid. During hydrolysis of the ghee, many triglyceride pockets are formed which can hold the active ingredients in the decoctions in combination as well as individually. This means that the active ingredients may act synergistically as well as individually. In addition, additives including one or more of vitamins A, C, D and E may be added.

For psoriatic patients who are on methotrexate, a decoction or powder of *Psoralea corylisfolia* may be included in the cream.

The cream of this embodiment of the invention provides relief of skin dryness, inflammation, irritation, rashes, papules, abrasions and discolouration. The cream should not be taken by mouth and should be kept out of the reach of children.

An alternative embodiment of the present invention is a cream made up as follows:

| | |
|---|---|
| Ghee | 3 kg |
| Water (boiled and cooled) | 1 kg |
| Decoction of *Centratherum anthelminthicum* (400 ml water + 40 g *Centratherum anthelminthicum*) | 400 ml |
| Decoction of Trifla (200 ml water + 20 g Trifla) | 200 ml |
| Decoction of *Berberis aristata* (100 ml water + 10 g *Berberis aristata*) | 100 ml |
| Fresh Juice of *Phyllanthus emblica* | 200 ml |
| Decoction of *Melia azadirachta* (100 ml water + 250 g *Melia azadirachta*) | 100 ml |

Trifla is a powder made up of extracts from *Terminalia chebula*, *Terminalia belerica* and *Phyllanthus emblica*.

To make up the cream, the ghee is first hydrolysed in a clean stainless steel vessel with one liter of water. Two to three days later, further hydrolysis should be effected with the decoction of *Centratherum anthelminthicum*. After a further two to three days, hydrolysis should be effected with the decoction of Trifla, followed two to three days later by further hydrolysis with the fresh juice of *Phyllanthus emblica*, and final hydrolysis two to three days later with the decoction of *Melia azadirachta*. The cream is ready when it becomes unable to assimilate any further liquid. During hydrolysis of the ghee, many triglyceride pockets are formed which can hold the active ingredients in the decoctions in combination as well as individually. This means that the active ingredients may act synergistically as well as individually. In addition, additives including one or more of vitamins A, C, D and E may be added.

For psoriatic patients who are on methotrexate, a decoction or powder of *Psoralea corylisfolia* may be included in the cream.

The cream of this embodiment of the invention provides relief of skin dryness, inflammation, irritation, rashes, papules, abrasions and discolouration. The cream should not be taken by mouth and should be kept out of the reach of children.

In a further alternative embodiment of the present invention there is provided a tea-bag containing:

| | |
|---|---|
| *Centratherum anthelminthicum* (fruit) | 20 g |
| Trifla (fruit) (Comprises equal parts of: | 10 g |
| *Phyllanthus emblica* *Terminalia chebula* *Terminalia belerica*) | |
| Trikatu (Comprises equal parts of: | 10 g |
| *Zingiber officinalis* (root) *Piper longum* (fruit) *Piper nigrum* (fruit)) | |

The ingredients are powdered and put into a tea-bag. Every day early in the morning one tea-bag should be placed into a container holding 150 ml of boiling water, covered with a lid, and allowed to stand for 10 minutes. The decoction should then be divided into three so as to provide three doses of 50 ml to be imbibed at six-hour intervals. The dosage of one tea bag per day is appropriate for an adult or adolescent weighing around 70 kg. For children of 6–7 years, the dosage should be halved. This provides a course of treatment for a first week.

This composition helps to relieve the irritation and itching cycle and also helps to relieve urticaria (the acute condition). For urticaria the dose may be raised to two tea-bags per day to provide six doses, one to be taken every three hours.

For the continued treatment, over a second week, of psoriasis, eczema and lichen planus, the composition of the tea-bag may be changed to:

| | |
|---|---|
| *Centratherum anthelminthicum* (fruit) | 10 g |
| Trifla (fruit) (Comprises equal parts of: | 10 g |
| *Phyllanthus emblica* *Terminalia chebula* *Terminalia balerica*) | |
| *Hemidesmus indicus* (roots) | 1 g |
| *Rubia cordifolia* (roots) | 2 g |
| *Tinospora cordifolia* (stem) | 0.5 g |
| *Berberis aristata* (roots) | 0.5 g |
| *Curcuma longa* (roots) | 2.5 g |
| *Smilex china* (roots) | 1 g |
| *Melia azadirachta* (bark) | 0.5 g |
| *Glycerhiza glabra* (stem) | 1 g |
| *Picrorhiza curroa* (stem) | 1 g |

The preparation and dosage is as for the course of treatment for the first week. This composition helps to relieve accumulated stress and inflammation and is additionally helpful for diabetic and/or hypertensive patients. It is also helpful in relieving urticaria and neurodermatitis. There are no apparent contraindications for pregnant patients. If necessary, treatment with this composition may be continued for up to six weeks.

*Glycerhiza glabra* and *Curcuma longa* are thought to have opposing actions, in that *Curcuma longa* is a drying agent whereas *Glycerhiza glabra* counters any over-drying effect. *Curcuma longa* is thought to be a keratolytic, anti-infective mild bactericidal, anti-inflammatory and mild anti-histaminic agent. When *Curcuma longa* is joined with *Centratherum anthelminthicum, Berberis aristata* and Trifla, the anti-histaminic and anti-inflammatory properties are enhanced. This combination is useful for both dry skin as well as weeping skin abrasions, discolouration of the skin, papules etc. The combination of tannins and other alkaloids is helpful in maintaining the normal texture of the skin, i.e. the normal thickness of the dermis and epidermis.

An alternative embodiment of the present invention, suitable as a night cream for psoriasis, as made up as follows:

| | |
|---|---|
| *Curcuma longa* | 15 g |
| *Curcuma aromatica* | 15 g |
| *Berberis aristata* | 15 g |
| *Terminalia chebula* | 10 g |
| *Phyllanthus emblica* | 10 g |
| *Terminalia belerica* | 10 g |

The ingredients are powdered and made into a fine paste by adding boiled, cooled water. The contents of the tea-bags of the previously described embodiments of the invention which were used for decoction are mixed with a small amount of this paste to provide a mixture to be applied to psoriatic patches.

This composition produces an anti-inflammatory effect, and is also useful in the treatment of psoriatic arthropathy.

A further embodiment of the present invention comprises a herbal coffee. It is now recognised that behavioural depression is a fairly common consequence of stress. It is also evident that an animal's ability to cope with stress largely influences the neurochemical consequences of stress. It is also recognised that exposure of living beings to inescapable and severe stress leads to depletion of adrenaline and serotonin, postulated to be the cause of endogenous depression.

A cup of ordinary coffee upon waking provides stimulation, but may be harmful when taken without milk and sugar throughout the rest of the day in order to combat tiredness.

The herbal coffee of this embodiment contains 25% coffee, 25% cardamon seeds and 50% a mixture of the following plants:

*Withenia somnifera dunal* (roots) (Indian ginseng)
*Asparagus racemosus* (roots)
*Tinospora cordifolia* (stem)
*Hemidesmus indicus* (roots)

10 g of the herbal coffee contains 2.5 g coffee, 2.5 g cardamon seeds, 2 g *Hemidesmus indicus*, 1 g *Withenia somnifera*, 1 g *Asparagus racemosus* and 1 g *Tinospora cordifolia*. A 10 g dose is to provide one cup of coffee once a day only. The course of treatment should not extend for more than three weeks at a time.

This herbal coffee is useful in combating stress and in the treatment of stress induced gastric ulcers.

In yet a further embodiment, the present invention provides a foundation cream made up as follows:

| | |
|---|---|
| Ghee | 3 kg |
| Water (boiled and cooled) | 2 l |
| Decoction of *Jasminum florum* (leaves) (200 g leaves) | 1 l |
| Sandalwood powder | 10 g |
| Sandalwood oil | 30 ml |
| or Rose oil | 30 ml |

The ghee is first hydrolysed with the water and then with a decoction of *Jasminum florum*. When trituration is complete, which may take 6–7 hours, the Sandalwood oil is added. After further trituration the Sandalwood powder is added, and the resulting cream thoroughly mixed.

This foundation cream is useful for protecting the skin from deleterious effects of physical and chemical agents. It is particularly useful for the treatment of skin which has been subjected to and damaged by lightening agents. The cream is also useful for the treatment of infantile eczema, skin care for diabetic patients and sunburn. For alleviating nappy rash in children and also for skincare in elderly people it can be mixed with castor oil and zinc ointment. The cream may also be used in the relief of postherpetic dermatitis and any sort of neurodermatitis. The cream should not be taken by mouth and should be kept out of reach of children.

The following table illustrates some of the properties found to be associated with the plants used in the present invention:

| | LATIN NAME | FAMILY IF KNOWN | CONSTITUENTS | PROPERTIES | POTENTIAL USES (OTHER THAN FOR SKIN DISORDERS) |
|---|---|---|---|---|---|
| 1 | Centratherum Anthelminticum | Compositeae | | Anti Histaminic | Decongestant Bactericidal Anti Parasitic Diuretic Anti Inflammatory Antipyretic Anti Obesity Colagogue Post Partum Period Anti Histaminic |
| 2 | Rubia Cordifolia | Rubiaceae | Anthraquinone | Immunomodulator Adrenocortical Stimuation Cortisol Preservation | Haemoglobinuria Erysepalas Blood Born Diseases |
| 3 | Hemidesmus Indicus | Asclepiadaleae | Triterpinoids Alkaloids of Indol Phenanthroidolidizine Pyridine groups Cardinoides Cyanogenetic Geycosides | | Rat Poisoning Bronchial Asthma Non Healing Ulcers Corneal Ulcer Neuritis Renal Stones |

-continued

| | LATIN NAME | FAMILY IF KNOWN | CONSTITUENTS | PROPERTIES | POTENTIAL USES (OTHER THAN FOR SKIN DISORDERS) |
|---|---|---|---|---|---|
| 4 | Berberes (Aristata)x Asiatica | Berberidaceae | Saponins<br>Tanins<br>Cyclitols<br>Berberine Alkaloids<br>Benzylisoquinoline<br>Bisbenzyliso-<br>quinoline<br>Aporphine | Anti-Inflammatory | Non healing ulcers<br>Jaundice<br>Leucorea<br>Diabetes Insepidus<br>Anti Pyretic<br>Spenic Enlargment<br>Liver Fluke Infestation<br>Abscess, Lymphangites<br>Lymphadenopathy<br>Ulces on varicose veins<br>Menorrhegia<br>Bleeding Piles |
| 5 | Curcuma Longa | Scitaminacea | Curcuminoids<br>Curcumin<br>Diferuloylmethane<br>Dicaffeol<br>Methane<br>Caffeoyl<br>Feruloyl<br>Methane Biogenesis<br>Phenyl Alanine<br>Malonate<br>Acetate<br>Sequiterpenes e.g.<br>Zingiberine 25%<br>Sesquiterpene alcohols<br>Ketones and Maloterpenes | Anti Histaminic<br>Anti Pruritic | Pain Killer<br>Decongestant<br>Diabetes Melitus<br>Diabetes Inspipedus<br>Neuro Dermatitis<br>Neuritis<br>Liver Protective<br>Helps in Liver problems<br>Prevention of Smallpox |
| 6 | Prunus Cerrasoides | Rosaceae | Kerneal Oil<br>Similar to bitter almonds<br>Amycedalin<br>Prulanrasin<br>Prunasin<br>D(-)Mandelonitrite-D Glucoside<br>Bitter Almond up to 1819 parts per million of CN<br>Wild cherry bark 5 parts per million of CN<br>Bark contains resin which yields the fluorescent compound Scopotin onhyderolysis<br>Benzoic acid<br>Trimethyl Galic acid<br>P-Cownaric Acid and sometamnin | Oxlhydrolysis yields Glucose<br>Benzyldehyde and Enzyme Prunase 0.07–0.16 per cent of Hydrocynic acid | Burning sensation<br>Antiemetic<br>Blood in vomiting (melory Weiss Syndrome)<br>Pyrexia of Unknown Origin |
| 7 | Tinospora Cordifolia | Menispemaeceae | Stem contains<br>Glycoside<br>Giolin<br>Nonglycoside<br>Gilenin and<br>Gliosterol | Anti spasmodic<br>Anti pyretic<br>Anti inflammatory<br>Hypoglycemic<br>Anti-allergic<br>Immuno Stimulant<br>Neutropenia produced by Cyclophosphamide was abolished by single dose of Tinospdra given before the cyclophosphamide given | General tonic<br>Diuretic Anhpyretic<br>Aphrodisiac<br>Effect In Jaundice<br>Diabetes Melitus<br>Anaemia Consumption<br>Emaciation<br>Infection |
| 8 | Picrorrhiza Kurroa | Scrophulaceae | Bitter Colycoside<br>Cathartic Acid<br>Picroside II (Iridoid-Glycosine)<br>Roots contain 60% of Picroside-I and Kutkoside in the ratio of 1:1.5 | Hepatoprotective Activity Against Carbon Tetrachloride and Galactosamine Induced Liver Damage | Heart Failure<br>Better Lactation<br>Skin Problems<br>Fever Hicough<br>Irritabl bowel syndrome<br>Helpful in Autoimmune Diseases |
| 9 | Psorelea Corylisfolia | Pappilionaceae | Seed Cake Rich in Nitrogen and Mineral Psoralish and Isopsoralin | Anti Immune Skin Diseases | Levcodernia Dental Caries Elephantiassis |

-continued

| | LATIN NAME | FAMILY IF KNOWN | CONSTITUENTS | PROPERTIES | POTENTIAL USES (OTHER THAN FOR SKIN DISORDERS) |
|---|---|---|---|---|---|
| 10 | Jasminum Grandiforum | | Fixed oil and Essential Oil Sponin Tanin Coumarins Iriboil Glycosides | | Renal stones Geographical tongue Wound Healing Syphilitic Ulcer |
| 11 | Melia Azardiracta | Meliaceae | | Anti Histaminic Immunomodulator | Urticaria Dandruf f Gout Cryoglobulenurca Lymphadenopathy Jaundice Haemetemesis Best Immunomodulator |
| 12 | Crataeva Nurvala | Capparidaceae | Saponin Like Sengka | Rubefacient Meant for Psoriatic Arthropathy Gouty Arthropathy Arthropathy due to cancer | Anti Pruritic Piles Renal Stones Lymphadenopathy Abscess Neuritia-Pain Hepatospenomegaly Obesity |
| 13 | Glyerrhyla Glabra | Pappilionaceae | Glycerrhizin | Immuno Modulator Enhances the production of Interferonyl in human peripheral lyniphocyte Macrophage cultures | Heart disease Picrorryza Kurroa Gout Anaemia Ullerative Colities Haemetamesis Hicough |
| 14 | Terminalia Chebula | Combretaceae | Shikinokic acid Gallic acid B-sitosterol daucosterol triacontanoic Palmitic acid Triethyl ester of chebulic acid ethyl ester of gallic acid by chemical and spectroscopic method | Useful in all diseases Useful in preparation of paste, cream, ointments Very useful for obstipation without any complications Useful in all diseases Useful in Ophthalmic problems (Decongestant) Helpful in ulcers Used in powdered medicines | 1. Bleeding piles 2. Diarrhoea due to indigestion 3. Abdominal problems 4. Diarrhoea due to irritable bowel syndrome 5. Anaemia due to hypothyroidism 6. Vomiting 7. Gout 8. Heavy legs 9. Hicough 10. Renal Stones 11. Haemetemesis 12. Melory Weiss Syndrome 13. Overdose of Nutmeg 14. Immunomodulator 15. Skin ulcers 16. Rheumatism |
| | Trifala Powder of Three Fruits | Combretaceae | | 1. Alcoholic extract of triphla exhibited Hypotensive effect in anaesthetised dog and cat 2. Contaction of isolated guini pig ileum and rabbit duodenum 3. -re ionotropic chronotropic effect 4. Anitflammatory and muscarisnic cholinoreceptor stimulating properties | |
| 14. 1. Terminalia Chebula | | Combretaceae | | | |
| 15. 2. Terminalia Belerica | | Combretaceae | | | |
| 16 3. Phylanthus Emblica | | Euphorbiaceae | | | |
| 17 | Aconitum Heterophyllum | Ranuncaulaceae | Root-Alkaloids Atisine Heterisine Histisine Heterophyllisine Heterophylline Heterphyllidine Atidine Hetidine Benzyl Heteratisine Dihydroastisine Hetisinone | | |

-continued

| | LATIN NAME | FAMILY IF KNOWN | CONSTITUENTS | PROPERTIES | POTENTIAL USES (OTHER THAN FOR SKIN DISORDERS) |
|---|---|---|---|---|---|
| 18 | Acorus Calamus | Araelae | | Marlotic<br>Antidote for Croton seed poisoning<br>Emetic<br>Antispasmodic<br>Insecticide | Epilepsy<br>Medicine for Memory<br>Cough-Lozenges |
| 19 | Piper Nigrum | Piperaceae | Piperine | Decongestant<br>Appetiser<br>Bactericidal<br>Pain Killer<br>Anti Histaminic | Cough Cold<br>Influenza<br>Hysteria<br>Diarrhoea<br>Night Blindness<br>Heart Diseases<br>Urticaria<br>Pyrexia of unknown origin<br>Arsenic poisoning<br>Anuria<br>Migraine<br>Lost Voice |
| 20 | Piper Longum | Piperaceae | Piplatrine<br>Fruit and roots both contain piplatrine | Anit Inflammatory<br>Anti spasmodic<br>Immunomodulator (Rasayana) | Cough<br>Gout<br>Pyrexia of unknown origin<br>Obesity<br>Piles<br>Worms<br>Diarrhoea<br>Erysepelas<br>Colagogue<br>Haemetemgis<br>Splenomegaly<br>Psiatica<br>Hicough |
| 21 | Zingiber Officinalis | Scitaminaceae | | Anti Histaminic<br>Anti Inflammatory | Painful Haematuria<br>Piles<br>Diarrhoea<br>Many chronic ailments<br>Intestinal obstruction<br>Appetiser<br>Jaundice<br>Rubefacient<br>Indigestion<br>Gout<br>Chronic dysentery<br>Irritable bowel syndrome<br>Hicough<br>Guline Barre Syndrome<br>Heart disease<br>Headache<br>Decongestant<br>Pyrexia of unknown origin<br>Urticaria<br>Intestial Colic |
| 22 | Holarrhena Antidysenterica | Apolynaceae | Conasin | Best Antidiarrhoeal | Paste used in application on any skin problems<br>Haemetemesis<br>Bleeding piles<br>Irritable Bowel Disease<br>Diarrhoea of TB patients<br>TB Lymphademisis<br>Renal Stones<br>Diabetes mellitus<br>Diabetes Insipedus<br>Phosphatwisa<br>Relieves Prusitis<br>Colagoyue<br>Immunomodulator for breast fed babies<br>Irritable Bowel Syndrome |
| 23 | Banhinia Variegata | Caesal Piniaceae | | Wound healing<br>Helpful in pain Anuria | Brain tonic<br>Piles<br>Haemetemisis<br>TB Lymphadenitis<br>Smallpox<br>Psoriatic<br>Arthropathy<br>Any skin problems |

What is claimed is:

1. A therapeutic composition comprising a therapeutically useful form of the plants *Melia azadirachta* and *Centratherum anthelminthicum*.

2. A composition as claimed in claim 1 further comprising a therapeutically useful form of at least one plant selected from the group consisting of *Phyllanthus emblica, Hemidesmus indicus, Tinospora cordifolia, Curcuma longa, Terminalia chebula, Terminalia belerica, Berberis aristata, Zingiber officinalis, Piper longum, Piper nigrum, Rubia cordifolia, Smilex china, Glycerhiza glabra, Picrorhiza curroa, Curcuma aromatica* and *Asparagus racemosus*.

3. A composition as claimed in claims 1 or 2, which further comprises coffee.

4. A composition as claimed in claims 1 or 2, which further comprises cardamon seeds.

5. A composition as claimed in claims 1 or 2, wherein the composition is formulated as an ointment or cream for topical application.

6. A composition as claimed in claim 5, wherein the therapeutically useful form of said plants includes ghee.

7. A composition as claimed in claims 1 or 2, wherein the composition is formulated in the manner of a tea-bag.

8. A composition as claimed in claims 1 or 2, wherein the composition is formulated in tablet form.

9. A therapeutic composition comprising a therapeutically useful form of the plant *Melia azadirachta* and further comprising a therapeutically useful form of at least one plant selected from the group consisting of *Phyllanthus emblica, Hemidesmus indicus, Tinospora cordifolia, Curcuma longa, Terminalia chebula, Terminalia belerica, Berberis aristata, Zingiber officinalis, Piper longum, Piper nigrum, Rubia cordifolia, Smilex china, Glycerhiza glabra, Picrorhiza curroa, Curcuma aromatic* and *Asparagus racemosus*.

10. A method of treating psoriasis through the administration to a human or animal body in need of such treatment of an effective amount of a therapeutically useful form of at least one member of the group consisting of the plants *Melia azadirachta* and *Centratherum anthelminthicum*.

11. A method of treating psoriasis through the administration to a human or animal body in need of such treatment of an effective amount of a therapeutically useful form of plants as claimed in claim 10, wherein the plants further comprise at least one plant selected from the group consisting of *Phyllanthus emblica, Hemidesmus indicus, Tinospora cordifolia, Curcuma longa, Terminalia chebula, Terminalia belerica, Berberis aristata, Zingiber officinalis, Piper longum, Piper nigrum, Rubia cordifolia, Smilex china, Glycerhiza glabra, Picrorhiza curroa, Curcuma aromatic* and *Asparagus racemosus*.

12. A method of treating eczema or lichen planus through the administration to a human or animal body in need of such treatment of an effective amount of a therapeutically useful form of at least one member of the group consisting of the plants *Melia azadirachta* and *Centratherum anthelminthicum*.

13. A method of treating eczema or lichen planus through the administration to a human or animal body in need of such treatment of an effective amount of a therapeutically useful form of plants as claimed in claim 12, wherein the plants further comprise at least one plant selected from the group consisting of *Phyllanthus emblica, Hemidesmus indicus, Tinospora cordifolia, Curcuma longa, Terminalia chebula, Terminalia belerica, Berberis aristata, Zingiber officinalis, Piper longum, Piper nigrum, Rubia cordifolia, Smilex china, Glycerhiza glabra, Picrorhiza curroa, Curcuma aromatic* and *Asparagus racemosus*.

* * * * *